United States Patent
Cheng et al.

(10) Patent No.: US 10,993,976 B2
(45) Date of Patent: *May 4, 2021

(54) MEDICAMENT FOR TREATING UREMIA AND PROTEINURIA

(71) Applicant: Shandong Zhonghai Pharmaceutical CO. LTD, Weifang (CN)

(72) Inventors: Qian Cheng, Weifang (CN); Baozhen Xu, Weifang (CN); Long Cheng, Weifang (CN)

(73) Assignee: SHANDONG ZHONGHAI PHARMACEUTICAL CO. LTD, Weifang (CN)

( * ) Notice: Subject to any disclaimer, the term of this patent is extended or adjusted under 35 U.S.C. 154(b) by 246 days.

This patent is subject to a terminal disclaimer.

(21) Appl. No.: 16/073,830

(22) PCT Filed: Jan. 20, 2017

(86) PCT No.: PCT/CN2017/071826
§ 371 (c)(1),
(2) Date: Jul. 30, 2018

(87) PCT Pub. No.: WO2017/129054
PCT Pub. Date: Aug. 3, 2017

(65) Prior Publication Data
US 2019/0038686 A1   Feb. 7, 2019

(30) Foreign Application Priority Data

Jan. 29, 2016 (CN) .......................... 201610061752.8

(51) Int. Cl.
| | | |
|---|---|---|
| *A61K 38/16* | (2006.01) | |
| *A61K 36/02* | (2006.01) | |
| *A61K 31/7012* | (2006.01) | |
| *A61K 36/315* | (2006.01) | |
| *A61K 31/7016* | (2006.01) | |
| *A61K 31/715* | (2006.01) | |
| *A61K 38/00* | (2006.01) | |
| *A61K 36/505* | (2006.01) | |
| *A61K 36/05* | (2006.01) | |
| *A61P 13/02* | (2006.01) | |
| *A61K 31/404* | (2006.01) | |
| *A61K 36/03* | (2006.01) | |
| *A61K 36/04* | (2006.01) | |

(52) U.S. Cl.
CPC ............ *A61K 36/02* (2013.01); *A61K 31/404* (2013.01); *A61K 31/7012* (2013.01); *A61K 31/7016* (2013.01); *A61K 31/715* (2013.01); *A61K 36/03* (2013.01); *A61K 36/04* (2013.01); *A61K 36/05* (2013.01); *A61K 36/315* (2013.01); *A61K 36/505* (2013.01); *A61K 38/00* (2013.01); *A61P 13/02* (2018.01)

(58) Field of Classification Search
CPC .................................................. A61K 38/168
See application file for complete search history.

(56) References Cited

U.S. PATENT DOCUMENTS 5,008,243 A * 4/1991 Ikuzawa .............. C07K 14/375
435/71.1

FOREIGN PATENT DOCUMENTS

| | | |
|---|---|---|
| CN | 1045586 A | 9/1990 |
| CN | 1129109 A | 8/1996 |
| CN | 102319256 B | 9/2014 |
| CN | 105597080 A | 5/2016 |
| KR | 100826560 B1 | 4/2008 |

OTHER PUBLICATIONS

Domozych et al., "The comparative aspects of cell wall chemistry in the green algae (Chlorophyta)," J Mol Evol 15:1-12, 1980.*
Go,H. et al., "A Glycoprotein from Laminaria Japonica Induces Apoptosis in HT-29 Colon Cancer Cells", Toxicology in Vitro, vol. 24, No. 6, Sep. 30, 2010 (Sep. 30, 2010), pp. 1546-1553, see abstract.

\* cited by examiner

*Primary Examiner* — Rosanne Kosson
(74) *Attorney, Agent, or Firm* — Bayramoglu Law Offices LLC

(57) ABSTRACT

A medicament for use in treating uremia and proteinuria, the medicament being a glycoprotein, a mixture of polysaccharide and protein, a polypeptide or a protein.

9 Claims, No Drawings

MEDICAMENT FOR TREATING UREMIA AND PROTEINURIA

CROSS REFERENCE TO RELATED APPLICATIONS

This application is the national phase entry of International Application No. PCT/CN2017/071826, filed on Jan. 20, 2017, which is based upon and claims priority to Chinese Patent Application No. 201610061752.8, filed on Jan. 29, 2016, the entire contents of which are incorporated herein by reference

TECHNICAL FIELD

The present invention relates to a medicament for use in treating uremia and urine protein diseases, and belongs to the field of medical technology.

BACKGROUND

Chronic renal failure (CRF) refers to a clinical syndrome that consists of progressive irreversible decline in renal function resulting from various kinds of renal diseases until emerging a series of symptoms and metabolic disorders due to loss of function. CRF is short for chronic renal failure. The end stage of chronic renal failure is commonly known as uremia. Uremia is not an independent disease, but a common clinical syndrome of various advanced kidney diseases. It is a syndrome consisting of a series of clinical manifestations of chronic renal failure when it enters the end stage.

Kidney disease is a common clinical disease and a frequently-occurring disease. In recent years, the incidence has the tendency of increasing gradually, which is very harmful to the health of the people. A variety of kidney diseases will finally develop into chronic renal failure (CRF) leading to a significant decrease in nephron and resulting in disorders in excretion of metabolites, regulation of water and lectrolyte balance, etc. The prognosis is very serious. At present, the main methods of western medicine in the treatment of CRF patients with uremia are dialysis and kidney transplantation. However, for the early and middle stage of CRF, there are no special medicaments, mostly passive symptomatic treatment which can not effectively control the development of CRF.

SUMMARY

The present invention provides a medicament for use in treating uremia and proteinuria in order to solve the deficiencies in the prior art for the purpose to achieve the following objectives hereof:
(1) The medicament hereof has a good therapeutic effect on uremia and urinary protein, with a total effective rate up to 84-94%.
(2) The medicament hereof reduces the toxins in the body of patients with uremia and urine protein and significantly deceases the contents of SCr, urine protein and blood urea nitrogen.
(3) The medicament hereof improves the nutritional status of the body and raises the contents of plasma albumin (Alb) and hemoglobin (Hb).
(4) The medicament hereof improves the hemorheological status and reduces the contents of coagulation factor I and whole blood viscosity.

In order to solve the aforesaid problems, the present invention adopts the following technical solution:

A medicament for use in treating uremia and urine protein, characterized in that the medicament is a glycoprotein, or a mixture of polysaccharides and proteins, or a polypeptide or protein; the glycoprotein comprises, by weight content, 1-99% sugar and 1-99% protein; the mixture of polysaccharides and proteins, by weight content, 1-99% polysaccharide and 1-99% protein. The said glycoprotein has a molecular weight of 0.2-3000 kDa;

The following are further modifications to the above technical solution:

The medicament is a marine algal glycoprotein.

The marine algal glycoprotein comprises, by weight content, 1-99% sugar and 1-99% protein; the mixture of marine algal polysaccharide and protein, by weight content, comprises 1-99% sugar and 1-99% protein.

The marine algal glycoprotein has a molecular weight of 0.2-3000 kDa; the marine algal as for the mixture of polysaccharide and the protein, a molecular weight of the polysaccharide is 0.2-3000 kDa and the protein has a molecular weight of 0.2-3000 kDa.

The said medicament comprises, by weight content, 1-99 portions of glycoprotein and 1-25 portions of glucuronic acid.

The said medicament comprises, by weight content, 1-99 portions of marine algalglycoprotein and 1-30 portions of glucuronic acid.

The said medicament comprises, by weight content, 1-99 portions of marine algalglycoprotein, 1-30 portions of glucuronic acid and 2-14 portions of natural indigo.

The said algae comprises one or more kinds of blue algae, green algae, red algae, gold algae, and brown algae.

The said medicament comprises, by weight content, 1-99 portions of marine algal glycoprotein, 4-16 portions of natural indigo, 7-15 portions of rhizome corydalis and 1-15 portions of glucuronic acid.

The said medicament comprises, by weight content, 1-99 portions of marine algal glycoproteins, 4-16 portions of natural indigo, 7-15 portions of rhizome corydalis and 8-13 portions of *Cyrtomium fortunei*.

The said medicament comprises, by weight content, 1-99% sugar and 1-99% protein.

The said marine algal glycoprotein comprises, by weight content, 1-99% sugar and 1-99% protein.

Compared with the prior art, the advantages of the present invention are:
(1) The medicament hereof has a good treatment effect on uremia and urine protein. Among those 50 patients, 20-23 patients are effective, 22-26 for responding and 3-8 for ineffective after three courses of treatment, with a total effective rate of 84-94%.
(2) The medicament hereof reduces toxins of uremia and urine protein; significantly reduces the contents of SCr, urine protein and blood urea nitrogen. After three courses of treatment, the level of SCr is 282.4-290 μmol/L, 2.42-2.54 g/24 h for urine protein and 14.2-15.0 mmol/L for blood urea nitrogen.
(3) The medicament hereof improves the nutritional status of the body and raises the contents of plasma albumin (Alb) and hemoglobin (Hb). After three courses of treatment, the level of Alb is 31.2-32.2 g/L and 84.2-85.7 g/L for Hb.
(4) The medicament hereof improves the hemorheological status. After three courses of treatment, the level of coagulation factor I is 3.75-3.82 g/L and the whole blood viscosity is 4.80-4.90.

DETAILED DESCRIPTION

The preferred embodiments of the present invention are described in the following, and the preferred embodiments described herein are only intended to illustrate and explain the invention, but not limited to this invention.

Embodiment 1 a Medicament for Use in Treating Uremia and Proteinuria

Wherein the medicament is a marine algal glycoprotein;
The said marine algal glycoprotein comprises, by weight content, 1% sugar and 99% protein.
The molecular weight is 0.2 kDa;
The said sugar is a polysaccharide;
The marine algae is blue algae;
The said polysaccharide comprises: glucose, galactose, mannose and rhamnose;
The said protein comprises: arginine, lysine, serine, and threonine;

Embodiment 2 a Medicament for Use in Treating Uremia and Proteinuria

Wherein the medicament is a marine algal glycoprotein;
The said marine algal glycoprotein comprises, by weight content, 7% sugar and 88% protein;
The molecular weight is 19 kDa;
The said sugar is a polysaccharide;
The said marine algae is green algae;
The said polysaccharide comprises: glucose, galactose, mannose and rhamnose;
The said protein comprises: arginine, lysine, serine, and threonine;

Embodiment 3 a Medicament for Use in Treating Uremia and Proteinuria

Wherein the medicament is a marine algal glycoprotein;
The said marine algal glycoprotein comprises, by weight content, 22% sugar and 72% protein,
The molecular weight is 5 kDa;
The said sugar is a polysaccharide;
The marine algae is blue algae;
The said polysaccharide comprises: glucose, galactose, mannose and rhamnose;
The said protein comprises: arginine, lysine, serine, and threonine;

Embodiment 4 a Medicament for Use in Treating Uremia and Proteinuria

Wherein the medicament is a marine algal glycoprotein;
The said marine algal glycoprotein comprises, by weight content, 37% sugar and 53% protein;
The molecular weight is 100 kDa;
The said sugar is a polysaccharide;
The said marine algae is red algae;
The said polysaccharide comprises: glucose, galactose, mannose and rhamnose;
The said protein comprises: arginine, lysine, serine, and threonine;

Embodiment 5 a Medicament for Use in Treating Uremia and Proteinuria

Wherein the medicament is a marine algal glycoprotein;
The said marine algal glycoprotein comprises, by weight content, 63% sugar and 30% protein;
The molecular weight is 800 kDa;
The said sugar is a polysaccharide;
The marine algae is brown algaee;
The said polysaccharide comprises: glucose, galactose, mannose and rhamnose;
The said protein comprises: arginine, lysine, serine, and threonine;

Embodiment 6 a Medicament for Use in Treating Uremia and Proteinuria

Wherein the medicament is a marine algal glycoprotein;
The said marine algal glycoprotein comprises, by weight content, 99% sugar and 1% protein,
The molecular weight is 3000 kDa;
The said sugar is a polysaccharide;
The marine algae is gold algae;
The said polysaccharide comprises: glucose, galactose, mannose and rhamnose;
The said protein comprises: arginine, lysine, serine, and threonine;

The glycoprotein said in these above embodiments 1-6 further includes a pigment; the said pigment is a natural pigment contained in algal substances.

These above embodiments 1-6 could be summarized as:
A Medicament for use in Treating Uremia and Proteinuria
The said medicament is a glycoprotein;
The said glycoprotein comprises, by weight content, 1-99% sugar and 1-99% protein;
The molecular weight is 0.2-30000 kDa;
The said sugar is a polysaccharide;
The said medicament comprises 20 synthetic glycoproteins, synthetic polysaccharides and proteins.
The said protein comprises 20 amino acids and 8 synthetic amino acids;
The preparation method of the said medicament: the glycoprotein is prepared into capsules and tablets etc. according to a conventional process; the mixture of the polysaccharide and the protein is prepared into capsules and tablets etc. according to a conventional process.

Embodiment 7: Application of the Said Medicament in Treating Uremia and Proteinuria Patient selection: choose the patient who is suffering from CRF of renal insufficiency at decompensation stage (The content of SCr is within the range of 186-442 umol/L) to study. The primary disease is chronic glomerulonephritis (CGN) and nephrotic syndrome (NS), except CRF caused by renal arteriosclerosis, diabetic nephropathy and renal cysts.

These investigated patients were randomly divided into groups, 50 patients in each group, aged 19-66 years (mean 44.6±12.6 years), with a course of disease 12-46 months (mean 22.6±8.6 months).

Treatment group 1-6: The patients in embodiment 1-6 received the medicament mentioned of the invention, with a dose of 3 g/day, three times a day.

Control group: The patients received the oral administration of coated aldehyde oxystarch 5 g-10 g, twice a day.

All groups were treated with 1 month as a course of treatment.

The patients stopped using Chinese and western medicine 2 weeks before treatment. The dose was gradually decreased in these the patients who were treated with hormone previously. They were given high quality low protein, low phosphorus and high calorie diet, correction of water and electrolyte disorders and acidosis, and anti-infection, in order to remove those reversible factors that may cause temporary renal dysfunction. Lotensin 5-20 mg was given to the patients with hypertension, once a day, or/and nifedipine 10-20 mg, three or four times a day.

All the patients in the treatment group received 3 courses of treatment, and were observed in SCr, blood urea nitrogen (BUN), plasma albumin (Alb), hemoglobin (Hb), 24 h urine protein and coagulation factor I (Fib) and whole blood viscosity.

X2 test was used for enumeration data and t test was used for measurement data.

TABLE 1

Overall treatment effect of the medicament of the invention

| | Markedly effective (case) | Effective (case) | Ineffective (case) | Total effective rate (%) |
|---|---|---|---|---|
| Contrast | 10 | 22 | 18 | 64 |
| Embodiment 1 | 21 | 25 | 4 | 92 |
| Embodiment 2 | 22 | 25 | 3 | 94 |
| Embodiment 3 | 23 | 24 | 3 | 94 |
| Embodiment 4 | 20 | 26 | 4 | 92 |
| Embodiment 5 | 22 | 23 | 5 | 90 |
| Embodiment 6 | 20 | 22 | 8 | 84 |

The medicament of the invention has a better therapeutic effect on uremia and urine protein. Among those 50 patients, 20-23 patients are effective, 22-26 for responding and 3-8 for ineffective, with a total effective rate of 84-94%.

TABLE 2

Effects of the medicament of the invention on reducing toxins of uremia and urine protein and improving the nutritional status of the body

| | SCr (μmol/L) | Urine protein (g/24 h) | Blood usea nitrogen (mmol/L) | Alb (g/L) | Hb (g/L) |
|---|---|---|---|---|---|
| Contrast | 298.5 ± 76.8 | 2.78 ± 1.59 | 16.0 ± 6.4 | 30.4 ± 3.0 | 82.4 ± 9.5 |
| Embodiment 1 | 290.2 ± 86.3 | 2.53 ± 1.52 | 15.0 ± 5.7 | 31.2 ± 3.1 | 84.6 ± 8.5 |
| Embodiment 2 | 289.6 ± 74.3 | 2.50 ± 1.54 | 14.9 ± 6.2 | 31.6 ± 3.3 | 84.3 ± 7.7 |
| Embodiment 3 | 282.4 ± 75.7 | 2.42 ± 1.43 | 14.2 ± 6.1 | 32.2 ± 3.2 | 85.7 ± 7.3 |
| Embodiment 4 | 289.4 ± 76.9 | 2.51 ± 1.47 | 14.3 ± 6.0 | 31.3 ± 3.3 | 84.9 ± 8.2 |
| Embodiment 5 | 289.7 ± 74.3 | 2.53 ± 1.53 | 14.5 ± 5.0 | 31.4 ± 3.5 | 84.3 ± 8.3 |
| Embodiment 6 | 288.3 ± 76.2 | 2.54 ± 1.49 | 14.8 ± 5.3 | 31.5 ± 2.9 | 84.2 ± 8.7 |

The medicament of the invention reduces toxins of uremia and urine protein; significantly decreases contents of SCr, urine protein and blood urea nitrogen. After three courses of treatment, the level of SCr is 282.4-290 μmol/L, 2.42-2.54 g/24 h for urine protein, and 14.2-15.0 mmol/L for blood urea nitrogen.

The medicament of the invention improves the nutritional status of the body and raises the contents of plasma albumin (Alb) and hemoglobin (Hb). After three courses of treatment, the level of Alb is 31.2-32.2 g/L and 84.2-85.7 g/L for Hb.

TABLE 3

Impacts of the medicament of the invention on hemorheology

| | Blood coagulation factor I g/L | Whole blood viscosity |
|---|---|---|
| Contrast | 3.88 ± 0.48 | 4.98 ± 1.0 |
| Embodiment 1 | 3.80 ± 0.38 | 4.86 ± 0.95 |
| Embodiment 2 | 3.78 ± 0.36 | 4.85 ± 0.96 |
| Embodiment 3 | 3.75 ± 0.35 | 4.80 ± 0.92 |
| Embodiment 4 | 3.77 ± 0.40 | 4.86 ± 0.94 |
| Embodiment 5 | 3.79 ± 0.41 | 4.89 ± 1.1 |
| Embodiment 6 | 3.82 ± 0.42 | 4.90 ± 1.14 |

The medicament of the invention improves hemorheological status. After three courses of treatment, the content of coagulation factor I is 3.75-3.82 g/L and 4.80-4.90 for whole blood viscosity.

Embodiment 8 a Medicament for Use in Treating Uremia and Proteinuria

It comprises, by weight content, the following components: 1 portions of marine algal glycoprotein and 1 portion of glucuronic acid.

The said marine algal glycoprotein comprises, by weight content, 9% sugar and 88% protein, The molecular weight is 14 kDa;

The said sugar is a polysaccharide;

The said marine algae is spirulina;

The said polysaccharide comprises: glucose, galactose, mannose and rhamnose;

The said protein comprises: arginine, lysine, serine, and threonine;

Embodiment 9 a Medicament for Use in Treating Uremia and Proteinuria

Like Embodiment 8, only the ratio of marine algal glycoprotein and glucuronic acid is changed as follows:

It comprises, by weight content, the following components:

33 portions of marine algal glycoprotein and 7 portions of glucuronic acid.

Embodiment 10 a Medicament for Use in Treating Uremia and Proteinuria

Like Embodiment 8, only the ratio of marine algal glycoprotein and glucuronic acid is changed as follows:

It comprises, by weight content, the following components:

64 portions of marine algal glycoprotein and 19 portions of glucuronic acid.

Embodiment 11 a Medicament for Use in Treating Uremia and Proteinuria

Same to the embodiment 8, the weight ratio of marine algae glycoproteins and glucuronic acid is changed to:

It comprises, by weight content, the following components:

99 portions of marine algal glycoprotein and 30 portions of glucuronic acid.

Embodiment 12 a Medicament for Use in Treating Uremia and Proteinuria

Measured by weight, it comprises the following components: 1 portion of marine algal glycoprotein, 1 portion of glucuronic acid and 2 portions of natural indigo.

The said marine algal glycoprotein comprises, by weight content, 18% sugar and 74% protein, The molecular weight is 22 kDa;

The said sugar is a polysaccharide;

The said marine algal glycoproteins is the chlorella;

The said polysaccharide comprises: glucose, galactose, mannose and rhamnose;

The said protein comprises: arginine, lysine, serine, and threonine;

Embodiment 13 a Medicament for Use in Treating Uremia and Proteinuria

Like Embodiment 12, only the ratio of marine algal glycoprotein, glucuronic acid and natural indigo is changed as follows:

It comprises, by weight content, the following components: 27 portions of marine algal glycoprotein, 9 portions of glucuronic acid and 5 portions of natural indigo.

Embodiment 14 a Medicament for Use in Treating Uremia and Proteinuria

Like Embodiment 12, only the ratio of marine algal glycoprotein, glucuronic acid and natural indigo is changed as follows:

It comprises, by weight content, the following components: 50 portions of marine algal glycoprotein, 21 portions of glucuronic acid and 9 portions of natural indigo.

Embodiment 15 a Medicament for Use in Treating Uremia and Proteinuria

Like Embodiment 12, only the ratio of marine algal glycoprotein, glucuronic acid and natural indigo is changed as follows:

It comprises, by weight content, the following components: 99 portions of marine algal glycoprotein, 30 portions of glucuronic acid and 14 portions of natural indigo.

Embodiment 8-Embodiment 15: Application of the Said Medicament in Treating Uremia and Proteinuria Using the test method said in Embodiment 7, the medicament said in Embodiment 8-Embodiment 15 in this invention groups have the following application effects:

TABLE 4

Overall treatment effects of the medicament of the invention

|  | Markedly effective (case) | Effective (case) | Ineffective (case) | Total effective rate (%) |
| --- | --- | --- | --- | --- |
| Contrast | 10 | 22 | 18 | 64 |
| Embodiment 8 | 23 | 23 | 4 | 92 |
| Embodiment 9 | 36 | 13 | 1 | 98 |
| Embodiment 10 | 23 | 24 | 3 | 94 |
| Embodiment 11 | 24 | 22 | 4 | 92 |
| Embodiment 12 | 22 | 24 | 4 | 92 |
| Embodiment 13 | 36 | 13 | 1 | 98 |
| Embodiment 14 | 22 | 25 | 3 | 94 |
| Embodiment 15 | 23 | 24 | 3 | 94 |

TABLE 5

Effects of the medicament of the invention on reducing toxins of uremia and urine protein and improving the nutritional status of the body

|  | SCr (μmol/L) | Urine protein (g/24 h) | Blood usea nitrogen (mmol/L) | Alb (g/L) | Hb (g/L) |
| --- | --- | --- | --- | --- | --- |
| Contrast | 298.5 ± 76.8 | 2.78 ± 1.59 | 16.0 ± 6.4 | 30.4 ± 3.0 | 82.4 ± 9.5 |
| Embodiment 8 | 280.2 ± 86.3 | 2.33 ± 1.51 | 14.5 ± 5.7 | 33.0 ± 3.1 | 86.6 ± 8.0 |
| Embodiment 9 | 257.8 ± 74.6 | 1.90 ± 1.57 | 13.0 ± 6.2 | 35.6 ± 3.3 | 91.3 ± 7.9 |
| Embodiment 10 | 281.4 ± 75.5 | 2.32 ± 1.48 | 14.6 ± 6.1 | 32.6 ± 3.0 | 86.7 ± 7.8 |
| Embodiment 11 | 280.4 ± 77.4 | 2.41 ± 1.44 | 14.3 ± 6.0 | 33.3 ± 3.0 | 87.9 ± 8.5 |
| Embodiment 12 | 280.7 ± 75.4 | 2.43 ± 1.50 | 14.4 ± 5.0 | 32.4 ± 3.2 | 87.3 ± 8.4 |
| Embodiment 13 | 258.3 ± 75.6 | 1.85 ± 1.46 | 13.2 ± 5.3 | 36.5 ± 2.7 | 92.2 ± 8.6 |
| Embodiment 14 | 281.2 ± 74.5 | 2.35 ± 1.50 | 14.4 ± 5.0 | 33.1 ± 3.3 | 87.7 ± 8.0 |
| Embodiment 15 | 280.7 ± 74.6 | 2.36 ± 1.48 | 14.4 ± 5.0 | 32.9 ± 3.1 | 87.8 ± 8.2 |

TABLE 6

Impacts of the medicament of the invention on hemorheology

|  | Blood coagulation factor I g/L | Whole blood viscosity |
| --- | --- | --- |
| Contrast | 3.88 ± 0.48 | 4.98 ± 1.0 |
| Embodiment 8 | 3.74 ± 0.33 | 4.56 ± 0.90 |
| Embodiment 9 | 3.50 ± 0.34 | 4.35 ± 0.92 |
| Embodiment 10 | 3.72 ± 0.32 | 4.50 ± 0.93 |
| Embodiment 11 | 3.73 ± 0.40 | 4.56 ± 0.94 |
| Embodiment 12 | 3.71 ± 0.35 | 4.58 ± 1.0 |
| Embodiment 13 | 3.47 ± 0.32 | 4.32 ± 1.04 |

TABLE 6-continued

Impacts of the medicament of the invention on hemorheology

|  | Blood coagulation factor I g/L | Whole blood viscosity |
|---|---|---|
| Embodiment 14 | 3.70 ± 0.43 | 4.50 ± 0.95 |
| Embodiment 15 | 3.72 ± 0.42 | 4.52 ± 0.97 |

Embodiments 8-11 only change the weight ratio of marine algal glycoprotein and glucuronic acid.

According to the experimental effect, the embodiment 9 is the most preferably.

Embodiments 12-15 only change the weight ratio of marine algal glycoprotein, glucuronic acid and natural indigo. According to the experimental effect, the embodiment 13 is the most preferably.

Embodiment 16 a Medicament for Use in Treating Uremia and Proteinuria

It comprises, by weight content, the following components:

1 portion of marine algal glycoprotein, 4 portions of natural indigo, 7 portions of red bean, and 1 portion of glucuronic acid.

The marine algal glycoprotein comprises, by weight content, 26% sugar and 74% protein;

The molecular weight is 6 kDa;

The marine algae is blue algae;

The said polysaccharide comprises: glucose, galactose, mannose and rhamnose;

The said protein comprises: arginine, lysine, serine, and threonine;

Embodiment 17 a Medicament for Use in Treating Uremia and Proteinuria

Like Embodiment 16, only the ratio of marine algal glycoprotein, Corydalis ambigua Ch., glucuronic acid and natural indigo is changed as follows:

It comprises, by weight content, the following components:

43 portions of marine algal glycoprotein, 6 portions of natural indigo, 12 portions of rhizome corydalis and 11 portion of glucuronic acid.

Embodiment 16 a Medicament for Use in Treating Uremia and Proteinuria

Same to the embodiment 16, only the weight ratio of marine algal glycoproteins, natural indigo, rhizome corydalis and glucuronic acid is changed to:

It comprises, by weight content, the following components:

99 portions of marine algal glycoprotein, 16 portions of natural indigo, 15 portions of rhizome corydalis and 15 portions of glucuronic acid.

Embodiment 16 a Medicament for Use in Treating Uremia and Proteinuria

It comprises, by weight content, the following components:

1 portion of marine algal glycoprotein, 4 portions of natural indigo, 7 portions of rhizome corydalis and 8 portions of Cyrtomium fortunei.

The said marine algal glycoprotein comprises, by weight content, 63% sugar and 30% protein;

The molecular weight is 200 kDa;

The said sugar is a polysaccharide;

The said marine algae is blue algae;

The said polysaccharide comprises: glucose, galactose, mannose and rhamnose;

The said protein comprises: arginine, lysine, serine, and threonine;

Embodiment 17 a Medicament for Use in Treating Uremia and Proteinuria

Same to the embodiment 19, only the weight ratio of marine algal glycoproteins, natural indigo, rhizome corydalis and *Cyrtomium fortunei* is changed to:

It comprises, by weight content, the following components:

56 portions of marine algal glycoprotein, 13 portions of natural indigo, 11 portions of rhizome corydalis and 9 portions of *Cyrtomium fortunei*.

Embodiment 16 a Medicament for Use in Treating Uremia and Proteinuria

Same to the embodiment 19, only the weight ratio of marine algal glycoproteins, natural indigo, rhizome corydalis and *Cyrtomium fortunei* is changed to:

It comprises, by weight content, the following components:

99 portions of marine algal glycoprotein, 16 portions of natural indigo, 15 portions of rhizome corydalis and 13 portions of *Cyrtomium fortunei*.

Application of the Said Medicament in Embodiment 16-Embodiment 21 in Treating Uremia and Urine Protein:

Using the test method said in Embodiment 7, the medicament said in Embodiment 16-Embodiment 21 in this invention groups have the following application effects:

TABLE 7

Overall treatment effect of the medicament of the invention

|  | Markedly effective (case) | Effective (case) | Ineffective (case) | Total effective rate (%) |
|---|---|---|---|---|
| Contrast | 10 | 22 | 18 | 64 |
| Embodiment 16 | 25 | 22 | 3 | 94 |
| Embodiment 17 | 37 | 12 | 1 | 98 |
| Embodiment 18 | 26 | 21 | 3 | 94 |
| Embodiment 19 | 24 | 22 | 4 | 92 |
| Embodiment 20 | 38 | 11 | 1 | 98 |
| Embodiment 21 | 25 | 22 | 3 | 94 |

TABLE 8

Effects of the medicament of the invention on reducing toxins of uremia
and urine protein and improving the nutritional status of the body

|  | SCr (μmol/L) | Urine protein (g/24 h) | Blood usea nitrogen (mmol/L) | Alb (g/L) | Hb (g/L) |
|---|---|---|---|---|---|
| Contrast | 298.5 ± 76.8 | 2.78 ± 1.59 | 16.0 ± 6.4 | 30.4 ± 3.0 | 82.4 ± 9.5 |
| Embodiment 16 | 275.2 ± 80.3 | 2.20 ± 1.41 | 14.0 ± 5.8 | 33.3 ± 3.1 | 88.6 ± 8.0 |
| Embodiment 17 | 250.8 ± 75.6 | 1.87 ± 1.47 | 12.4 ± 6.0 | 36.8 ± 3.3 | 92.8 ± 7.2 |
| Embodiment 18 | 276.4 ± 74.5 | 2.22 ± 1.42 | 14.1 ± 5.8 | 32.2 ± 3.0 | 87.7 ± 7.5 |
| Embodiment 19 | 280.4 ± 73.4 | 2.21 ± 1.48 | 14.2 ± 6.2 | 33.1 ± 3.0 | 88.2 ± 8.0 |
| Embodiment 20 | 248.0 ± 72.6 | 1.85 ± 1.50 | 12.1 ± 5.8 | 36.5 ± 3.2 | 92.7 ± 8.1 |
| Embodiment 21 | 277.3 ± 74.3 | 2.19 ± 1.45 | 13.9 ± 5.3 | 33.0 ± 2.7 | 87.9 ± 8.6 |

TABLE 9

Effects of the medicament of the invention on hemorheology

|  | Blood coagulation factor I g/L | Whole blood viscosity |
|---|---|---|
| Contrast | 3.88 ± 0.48 | 4.98 ± 1.0 |
| Embodiment 16 | 3.70 ± 0.33 | 4.50 ± 0.80 |
| Embodiment 17 | 3.46 ± 0.34 | 4.30 ± 0.82 |
| Embodiment 18 | 3.65 ± 0.32 | 4.51 ± 0.83 |
| Embodiment 19 | 3.68 ± 0.40 | 4.53 ± 0.84 |
| Embodiment 20 | 3.43 ± 0.35 | 4.33 ± 0.95 |
| Embodiment 21 | 3.69 ± 0.32 | 4.50 ± 0.93 |

In the embodiments 16-18, only the weight ratio of marine algal glycoproteins, natural indigo, rhizome corydalis and glucuronic acid is changed. According to the experimental effect, the embodiment 17 is the most preferably.

In the embodiments 19-21, only the weight ratio of marine algal glycoproteins, natural indigo, rhizome corydalis and *Cyrtomium fortunei* is changed. According to the experimental effect, the embodiment 20 is the most preferably.

Embodiment 22 a Medicament for Use in Treating Uremia and Proteinuria

It comprises, by weight content, the following components:

80 portions of marine algal glycoprotein, 10 portions of flavescent sophora root, 5 portions of auckandia root, 5 portions of purple azalea, 7 portions of unispike kyllinga herb, 8 portions of evodia fruit, 10 portions of pyrola herb, 8 portions of *Cuscuta chinensis* and 6 portions of solomon's seal.

The said marine algal glycoprotein comprises, by weight content, 10% sugar and 85% protein, The molecular weight is 15 kDa;

The said marine algal glycoprotein is the chlorella;

The said sugar, by weight content, comprises the following components: 8 portions of glucose, 5 portions of galactose, and 11 portions of carubinose;

The protein mentioned, by weight content, comprises the following components: 7 portions of serine, 9 portions of threonine and 15 portions of hydroxylysine.

Embodiment 22 a Medicament for Use in Treating Uremia and Proteinuria

It comprises, by weight content, the following components:

75 portions of marine algal glycoproteins, 10 portions of epimedium, 8 portions of cardamom, 7 portions of gallnut, 9 portions of radix aconiti lateralis preparata, 6 portions of gastrodia, 5 portions of caulis sinomenii, 6 portions of lotus leaves and 3 portions of broadleaf holly leaves;

The said marine algal glycoprotein comprises, by weight content, 60% sugar and 25% protein, The molecular weight is 18 kDa;

The marine algae is synuraceae urelin;

The said sugar, by weight content, comprises the following components: 20 portions of glucose, 8 portions of galactose, and 15 portions of carubinose;

The protein mentioned, measured by weight, comprises the following components: 10 portions of serine, 15 portions of threonine and 17 portions of hydroxylysine.

Embodiment 24 the Preparation Method of a Medicament for Use in Treating Uremia and Proteinuria Step 1: Weighing Weigh the marine algal glycoprotein and all Chinese medicine components according to the formula;

Step 2: Extraction of Chinese Medicine (1) Washing

Wash all Chinese medicine components with clear water, and remove the impurities;

(2) Crash and Microwave Extraction

The Chinese medicine is pulverized into 100-mesh medicinal material powder, 8 times of 50% ethanol is added, the temperature is controlled at 60° C., microwave radiation is performed at the microwave irradiation of 260 W, microwave wavelength of 130 mm, a frequency of 1200 MHz for 5 min, then filtration is carried out, and finally the filtrate is collected;

The medicine dregs are separated, 6 times of clear water is added, the temperature is controlled at 50° C., microwave radiation is performed at the microwave irradiation of 200 W, microwave wavelength of 1430 mm, a frequency of 1250 MHz for 5 min, then filtration is carried out, and finally the filtrate is collected;

Pool the filtrate collected from the two procedures; atomize and dry to prepare them into Chinese medicine powder;

Step 3 Add Marine Algal Glycoprotein.

Marine algal glycoprotein powder is combined with the above-mentioned prepared Chinese medicine powder and mixed together to make the capsules, tablets and other preparations.

The Application of Medicaments Above-Mentioned in Embodiments 22 and 23 the Treatment of Uremia and Urine Protein Using the test method said in Embodiment 7, the medicament said in Embodiment 22-Embodiment 23 in this invention groups have the following application effects:

TABLE 10

Overall treatment effect of the medicament of the invention

|  | Markedly effective (case) | Effective (case) | Ineffective (case) | Total effective rate (%) |
|---|---|---|---|---|
| Contrast | 10 | 22 | 18 | 64 |
| Embodiment 22 | 39 | 10 | 1 | 98 |
| Embodiment 23 | 38 | 11 | 1 | 98 |

TABLE 11

Effects of the medicament of the invention on reducing toxins of uremia and urine protein and improving the nutritional status of the body

|  | SCr ($\mu$mol/L) | Urine protein (g/24 h) | Blood usea nitrogen (mmol/L) | Alb (g/L) | Hb (g/L) |
|---|---|---|---|---|---|
| Contrast | 298.5 ± 76.8 | 2.78 ± 1.59 | 16.0 ± 6.4 | 30.4 ± 3.0 | 82.4 ± 9.5 |
| Embodiment 22 | 245.2 ± 76.7 | 1.82 ± 1.41 | 12.0 ± 5.8 | 36.9 ± 3.1 | 93.1 ± 7.4 |
| Embodiment 23 | 255.8 ± 75.6 | 1.98 ± 1.42 | 13.2 ± 5.5 | 35.2 ± 3.3 | 91.9 ± 7.3 |

TABLE 12

Impacts of the medicament of the invention on hemorheology

|  | Blood coagulation factor I g/L | Whole blood viscosity |
|---|---|---|
| Contrast | 3.88 ± 0.48 | 4.98 ± 1.0 |
| Embodiment 22 | 3.43 ± 0.30 | 4.32 ± 0.70 |
| Embodiment 23 | 3.56 ± 0.32 | 4.40 ± 0.72 |

The medicaments thereof have a pH of between 5.3 and 9.8, preferably between 6.5 and 7.5.

The invention has been subjected to a large number of experiments, and we have carried out multiple tests using a mixture of marine shells, bones of livestock and poultry, a mixture of glycoprotein, polysaccharides and proteins extracted from the skeleton of marine animals, and the objectives of the invention have also been achieved.

Embodiment 25, a Medicament for the Treatment of Uremia and Urine Protein

The said medicament is a mixture of polysaccharides and proteins;

The said medicament comprises, by weight content portions, 1-99% polysaccharide and 1-99% protein.

The said polysaccharide comprises: glucose, galactose, mannose and rhamnose;

The said protein comprises: Asparagine, cysteine, lysine, arginine, serine, threonine, alanine, aspartic acid, glutamine, glutamic acid, histidine, isoleucine, glycine Leucine, methionine, phenylalanine, valine, tyrosine, and valine.

As for the said mixture of polysaccharide and the protein, the polysaccharide has a molecular weight of 0.2-3000 kDa and the protein has a molecular weight of 0.2-3000 kDa.

The mixture of polysaccharides and proteins, further a mixture of algal polysaccharides and algal proteins;

A mixture of the algal polysaccharide and the algal protein also comprises a pigment;

The said pigment is a natural pigment contained in the algal substance;

The said algal protein may be phycocyanin, phycoerythrin or phycoerythrin.

The nontoxic reaction dose of the medicament mentioned of the invention by oral administration for 12 weeks is 1.6 g/kg in dogs, which is 50 times of the equivalent dose for human, therefore, the safety of clinical trial can be guaranteed.

The medicine described in the invention can also be a health care product or a food.

The basic principles and main features of the present invention and the advantages of the present invention are shown and described above. It should be understood by the technicians in this field that, the present invention is not limited by the foregoing embodiments, and that what are described in the aforementioned embodiments and instructions are only the principles of this invention; without departing from the spirit and scope of the invention, this invention may be subject to various changes and modifications, which will be included within the scope of the invention as claimed. The scope of the invention is defined by the appended claims and their equivalents.

What is claimed is:

1. A medicament for use in treating uremia and proteinuria, wherein the medicament comprises 1-99 portions of a glycoprotein, 4-16 portions of natural indigo, 7-15 portions of Corydalis tuber and 1-15 portions of glucuronic acid by weight, wherein the amount of the glycoprotein is a therapeutically effective amount that treats uremia and proteinuria.

2. The medicament of claim 1, wherein the glycoprotein is a marine algal glycoprotein.

3. The medicament of claim 2, the marine algal glycoprotein comprises 1-99% sugar and 1-99% protein by weight.

4. The medicament of claim 2, the marine algal glycoprotein has a molecular weight of 0.2-3,000 kDa.

5. A medicament for use in treating uremia and proteinuria, wherein the medicament comprises 1-99 portions of 4 glycoprotein, 1-30 portions of glucuronic acid and 2-14 portions of natural indigo by weight, wherein the amount of the glycoprotein is a therapeutically effective amount that treats uremia and proteinuria.

6. The medicament of claim 2, wherein the marine algal glycoprotein comes from a marine alga that is selected from the group consisting of a spirulina, a green alga, a red alga, a gold alga and a brown alga.

7. The medicament of claim 1, further comprising 8-13 portions of *Cyrtomium fortunei* by weight.

8. The medicament of claim 5, wherein the glycoprotein comprises 1-99% sugar and 1-99% protein by weight.

9. The medicament of claim 7, wherein the glycoprotein comprises 1-99% sugar and 1-99% protein by weight.

* * * * *